United States Patent [19]
Vetrecin et al.

[11] Patent Number: 5,944,919
[45] Date of Patent: Aug. 31, 1999

[54] PROCESS FOR BLACKENING SURGICAL NEEDLES

[75] Inventors: Robert Vetrecin, Stewartsville, N.J.; Bruce Hersey, San Angelo, Tex.

[73] Assignee: Ethicon, Inc., Somerville, N.J.

[21] Appl. No.: 08/944,142

[22] Filed: Oct. 6, 1997

Related U.S. Application Data

[63] Continuation of application No. 08/622,794, Mar. 27, 1996, abandoned.

[51] Int. Cl.⁶ .................................................. C23C 8/10
[52] U.S. Cl. ........................ 148/280; 148/283; 148/284; 148/286; 148/287; 204/157.51; 422/23
[58] Field of Search ..................................... 148/280, 283, 148/284, 286, 287; 204/157.51; 422/23

[56] References Cited

U.S. PATENT DOCUMENTS

| | | | |
|---|---|---|---|
| 3,108,900 | 10/1963 | Papp | 117/93.1 |
| 3,851,436 | 12/1974 | Fraser et al. | 53/21 |
| 3,876,373 | 4/1975 | Glyptis | 21/54 |
| 3,948,601 | 4/1976 | Fraser et al. | 21/54 |
| 4,207,286 | 6/1980 | Gutboucher | 422/21 |
| 4,321,232 | 3/1982 | Bithell | 422/23 |
| 4,348,357 | 9/1982 | Bithell | 422/23 |
| 4,643,876 | 2/1987 | Jacobs et al. | 422/23 |
| 4,756,882 | 7/1988 | Jacobs et al. | 422/23 |
| 4,801,427 | 1/1989 | Jacob | 422/23 |
| 4,818,488 | 4/1989 | Jacob | 422/23 |
| 4,844,943 | 7/1989 | Chassagneux et al. | 427/34 |
| 4,898,715 | 2/1990 | Jacob | 422/186.29 |
| 4,909,995 | 3/1990 | Jacob | 422/186.29 |
| 4,917,586 | 4/1990 | Jacob | 422/21 |
| 4,931,261 | 6/1990 | Jacob | 422/292 |
| 4,943,417 | 7/1990 | Jacob | 422/292 |
| 4,976,920 | 12/1990 | Jacob | 422/23 |
| 5,011,660 | 4/1991 | Arena | 422/22 |
| 5,084,239 | 1/1992 | Moulton et al. | 422/22 |
| 5,087,418 | 2/1992 | Jacob | 422/23 |
| 5,115,166 | 5/1992 | Campbell et al. | 315/111.21 |
| 5,171,525 | 12/1992 | Jacob | 422/23 |
| 5,178,829 | 1/1993 | Moulton et al. | 422/23 |
| 5,186,893 | 2/1993 | Moulton et al. | 422/23 |
| 5,200,146 | 4/1993 | Goodman | 422/23 |
| 5,200,158 | 4/1993 | Jacob | 422/292 |
| 5,244,629 | 9/1993 | Caputo et al. | 422/22 |
| 5,262,125 | 11/1993 | Goodman | 422/23 |
| 5,288,460 | 2/1994 | Caputo et al. | 422/23 |
| 5,302,343 | 4/1994 | Jacob | 422/23 |
| 5,325,020 | 6/1994 | Campbell et al. | 315/111.21 |
| 5,328,524 | 7/1994 | Hertz | 148/241 |
| 5,370,694 | 12/1994 | Davidson | 633/16 |
| 5,384,167 | 1/1995 | Nishiwaki | 427/569 |
| 5,413,759 | 5/1995 | Campbell et al. | 422/23 |
| 5,466,424 | 11/1995 | Kusano | 427/569 |
| 5,510,158 | 4/1996 | Hiramoto | 427/582 |

OTHER PUBLICATIONS

Corrosion and Corrosion Control: An Introduction to Corrosion Science and Engineering; Herbert H. Uhlig; John Wiley & Sons, Inc., New York, 1963; pp. 67–70.

Plasma Cleaning, a Sensible Alternative to Wet Chemicals, Dr. Don Paguin; a Publication by GaSonics/IPC, Fort Washington, Pa.; 2 pages (No date).

Using RF Plasma to Improfe Potting and Coating, Edward M. Liston, GaSonics Applications Note, GaSonics International, San Jose, CA.; 4 pages (No Date).

Plasma Treatment for Improved Bonding: A Review, J. Adhesion, 1989, vol. 30, Edward M. Liston, pp. 199–218.

Practical Application of Plasma Surface Modification, Mark D. Smith, International Symposium Polymer Surface Modification: Relevance to Adhesion, Nov. 1993.

Improving Adhesion of Gimbal to Pad Bonding by Plasma Cleaning Stainless Steel Gilbal Spring.

Primary Examiner—David A. Simmons
Assistant Examiner—Robert R. Koehler
Attorney, Agent, or Firm—Emil Richard Skula

[57] ABSTRACT

A process for blackening the surfaces of a metal alloy surgical needle or a metal alloy surgical instrument. The process consists of exposing the surfaces of a metal alloy surgical needle or surgical instrument to a gaseous plasma for a sufficient amount of time to effectively blacken the surfaces of the needle or instrument.

20 Claims, 1 Drawing Sheet

PROCESS FOR BLACKENING SURGICAL NEEDLES

This is a continuation of application Ser. No. 08/622,794, filed Mar. 27, 1996, now abandoned.

TECHNICAL FIELD

The field of art to which this invention pertains is surgical needles, more specifically a method of blackening surgical needles.

BACKGROUND OF THE INVENTION

Surgical needles are typically manufactured from various grades of metal steel alloys which will not corrode when the needles are exposed to ambient environmental conditions after manufacture and prior to, and during, use. The metal alloys typically may include the Type 300 and 400 series stainless steels and other conventional alloys such as Types 455, 420, and 420F, and the like. In addition, martensitic stainless steel alloys containing nickel and titanium are useful such as those disclosed in U.S. Pat. No. 5,000,912 which is incorporated by reference. Surgical needles and processes for manufacturing surgical needles are disclosed in commonly assigned, co-pending U.S. patent application Ser. Nos. 08/405,554 and 08/429,446 which are incorporated by reference.

In certain surgical procedures, it is preferred to utilize surgical needles having a blackened exterior surface rather than needles having a bright shiney surface. It is believed that blackening is caused by a build up of oxide on the surface of the metal alloy needle or instrument. There are a number of known conventional processes for blackening stainless steel alloys and other conventional metal alloys including various chemical and electrochemical processes. Processes for blackening surgical needles are disclosed in U.S. Pat. Nos. 4,959,068 and 4,905,695 which are incorporated by reference.

The conventional blackening processes which are most typically used are a chemical blackening treatment and an electrochemical treatment. The chemical treatment utilizes mixtures of acids and aqueous salts to oxidize the surface of a surgical needle thereby producing an oxidized layer and blackening the needle. For example, a typically used chemical mixture will contain sulfuric acid and potassium dichromate in an aqueous bath. The aqueous bath is preferably maintained at room temperature although other temperatures may be utilized. Another type of blackening treatment is an electrochemical process. In an electrochemical blackening process needles are placed in a chemical bath and an electric current is passed through the bath. Such electrochemical processes typically utilize voltages in the range of, for example, 30 volts to about 150 volts and high amperages in a range of, for example, about 5 amps to about 175 amps.

Although the existing electrochemical and chemical blackening processes produce needles having adequately blackened surfaces, there are certain disadvantages associated with the use of these processes. The processes require the use of chemical baths generating both chemical fumes and hazardous waste. The chemical baths have a limited useable life and have to be disposed of at considerable expense. In addition the use of the types of chemicals required for chemical or electrochemical baths has attendant safety hazards which must be constantly monitored. Also, the electrochemical process uses relatively high voltages and amperages and, once again, considerable safety precautions must be taken to protect operators.

Accordingly there is a need in this art for a novel method of blackening metal alloy surgical needles and surgical instruments without the use of chemical or electrochemical processes.

DISCLOSURE OF THE INVENTION

Accordingly, it is an object of the present invention to provide a process for blackening the surfaces of metal alloy surgical needles and surgical instruments without the use of chemical baths.

It is yet a further object of the present invention to provide a method of blackening the surfaces of surgical needles and surgical instruments without the use of an electrochemical bath.

It is still yet a further object of the present invention to provide a method for blackening a metal alloy surgical needle or surgical instrument without the need for passing an electrical current through the needle or instrument.

Therefore, a process for blackening a metal alloy surgical needle or surgical instrument is disclosed. The metal surgical instrument or surgical needle has an exterior surface and, optionally, an inner surface. The surfaces of the metal surgical needle or surgical instrument are exposed to a gaseous plasma for a sufficient period of time at a sufficient temperature to effectively blacken the surfaces of the needle or instrument.

The novel method of blackening metal alloy surgical needles or surgical instruments of the present invention has many advantages. Environmental hazards associated with the use of chemical baths and electrochemical baths are eliminated since these chemical baths are not needed. In addition, the gaseous plasma which is used to blacken surfaces of the surgical instruments and the surgical needles may be recaptured and recycled after each process. Yet another advantage of the present invention is that the need for passing an electric current through the needles and the attendant safety hazards are eliminated.

The foregoing and other features and advantages of the present invention will become more apparent from the following description and accompanying drawings.

BEST MODE FOR CARRYING OUT THE INVENTION

Figure 1:
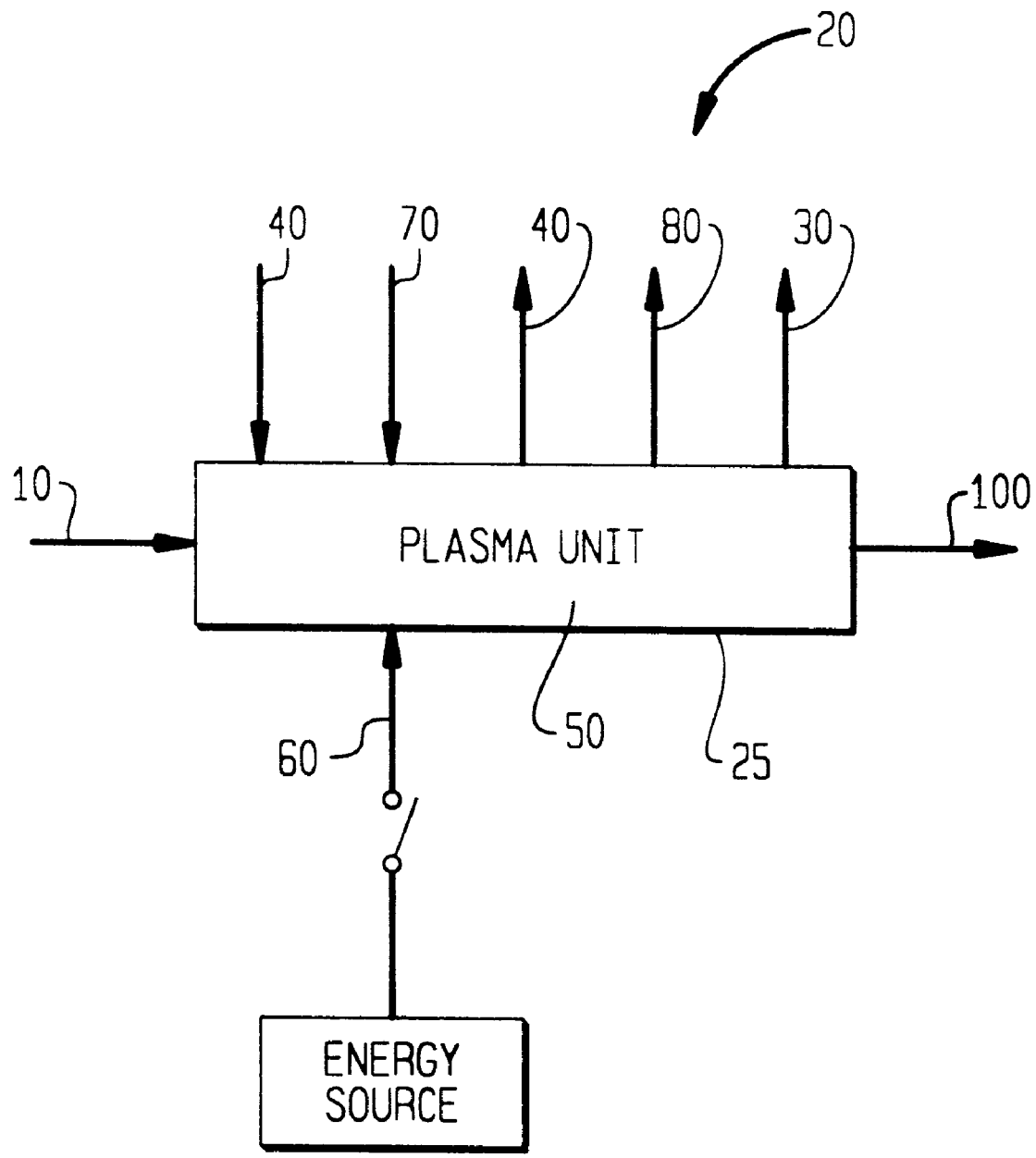
FIG. 1 illustrates a flow diagram for a blackening process of the present invention.

The gases which can be used for the plasmas of the present invention include oxygen, helium, carbon tetrafluoride, nitrogen, argon and the like and mixtures thereof and equivalents thereof. It is preferred to use mixtures of gases such as oxygen, helium, and carbon tetrafluoride. It is particularly preferred to use oxygen or a mixture of oxygen and carbon tetrafluoride or a mixture of oxygen and helium. When using a mixture of oxygen, helium and carbon tetrafluoride, sufficient amounts of each component will be utilized to provide an effective plasma mixture. Typically, about 50% to about 99% of oxygen will be used in such a mixture, more typically about 60% to about 99%, and preferably about 70% to about 99%. The typical amounts of helium which will be used in such a mixture will typically be about 1% to about 50%, more typically about 10% to about 40%, and preferably about 10% to about 30%. The amounts of carbon tetrafluoride which will be utilized in a preferred mixture will typically be about 1% to about 40%, more typically about 15% to about 35%, and preferably about 10% to about 30%. As previously mentioned, it is particularly preferred to use oxygen to form the plasma or a mixture of oxygen and helium or a mixture of oxygen and carbon tetrachloride. When using a mixture of oxygen and helium, about 50% to about 80% of oxygen will be used, preferably about 80%, and about 10% to about 50% of helium will be used, preferably about 20%. When using a mixture of oxygen and carbon tetrachloride, about 50% to about 80% of oxygen will be used, preferably about 80%, and about 10% to about 50% of carbon tetrachloride will be used, preferably about 20%. The percentages used herein are percentages by weight.

A conventional plasma treatment process unit is typically used in the processes of the present invention. The plasma unit will typically have a volumetric chamber which is capable of withstanding both pressure and vacuum. Mounted in the chamber will be at least one electrode. A preferred unit is a Gasonics® plasma unit manufactured by Gasonics/IPL, San Jose, Calif., however, any conventional or equivalent gas plasma unit may be utilized as well as any primary or secondary discharge unit. A gaseous mixture or gas is typically brought up to a plasma state in these units by exposing the gas to sufficient electromagnetic energy such as radio frequency electromagnetic waves, microwaves, etc., to effectively induce a plasma state. However, other means of exciting the gas into a plasma state may be utilized including direct current, laser energy, equivalents thereof and the like. If desired, the needles or surgical instruments can be exposed to a conventional plasma torch.

Sufficient electromagnetic energy will be applied to the gas to effectively produce a plasma condition. Typically the amount of energy utilized will be about 250 W (0.12 watts/$M^2$) to about 2500 W (1.2 watts/$M^2$), more typically to about 300 W (0.014 watts/$M^2$) to about 1000 W (0.46 watts/$M^2$), and preferably about 400 W (0.18 watts/$M^2$) to about 900 W (0.42 watts/$M^2$). Of course those skilled in the art will appreciate that the amount of energy utilized will vary in accordance with the process parameters including gas flow, gas type, electrode area, and vacuum, etc., as well as the type, size, condition and configuration of the plasma unit.

The gas will flow into the plasma treatment process unit at a sufficient volumetric flow rate to effectively produce a plasma. The volume of the chamber of the unit will be sufficient to effectively contain the needles or instruments being treated. These parameters will vary in accordance with the particular parameters of the process and are readily determined by those skilled in the art.

A typical flow diagram for a blackening process of the present invention is illustrated in FIG. 1, although those skilled in the art will appreciate that various steps may be eliminated or added to the processes of the present invention. As illustrated in FIG. 1, the initial step of such a process is to load needles or surgical instruments 10 into a chamber 25 of a plasma treatment unit 20. Next, a sufficient vacuum 30 is pulled on the chamber 25 to effectively evacuate the chamber of air and produce a sufficient vacuum to introduce the plasma. Typically, the vacuum may be about 0.05 to about 1 Torr, more typically about 0.25 to about 0.75 Torr, and preferably about 0.3 to about 0.5 Torr, however this will vary with the type and configuration of plasma unit utilized. Then, the chamber 25 is filled with a gas or gas mixture 40 of choice so that there is a sufficient amount of gas 40 present in the chamber 25 to effectively form the gas plasma 50. Typically the gas flow 40 utilized may be about 50 to about 500 cc/min, more typically about 100, to about 500 cc/min, and preferably about 200 to about 500 cc/min, however this flow rate may vary depending upon the type and configuration of the plasma unit utilized. Next the power is switched on to energize the energy source 60 thereby forming a plasma 50, and the needles or surgical instruments 10 are exposed to the gas plasma 50 for a sufficient period of time to effectively produce an effectively blackened, non-reflective coating on the surfaces of the needles or surgical instruments 10. Typically the plasma cycle time may be about 10 to about 120 minutes, more typically about 20 to about 40 minutes, and preferably about 30 to about 45 minutes, however, this will vary depending upon the process cycle, process parameters, and plasma unit type and configuration utilized. Next, the gas 40 is removed from chamber 25 through vent 80 and the chamber 25 is back-filled with an inert gas 70, such as nitrogen, and maintained at a sufficient pressure for a sufficient amount of time to effectively cool down the needles or instruments. For example, the needles or instruments 10 may be held in the cool down phase for about 3 to about 10 minutes, more typically about 3 to about 7 minutes, and preferably about 3 to about 5 minutes. The inert gas pressure may be, for example, about 0.05 Torr to about 1.0 Torr. Finally, the blackened needles or instruments 100 are removed from the chamber 25 of the gas plasma unit 20. The gas 40 removed through vent 80 may be recycled for use in the process.

The oxide layers produced by the plasma treatment blackening process of the present invention will be sufficient to effectively provide a conventional blue/black nonreflective coating to the surfaces of the needles or instruments 10. The exterior surfaces of needles or instruments 10 are typically blackened, however the interior surfaces may be blackened as well.

The surgical needles which can be blackened using the process of the present invention include any conventional surgical needle having a piercing point, sharp or blunt, and a suture mounting end. The suture mounting end may have a channel or a blind drilled hole for receiving sutures. The surgical instruments which may be blackened using the process of the present invention include conventional instruments and parts thereof such as needle graspers, scissors, forceps, scalpels, catheters, cutting instruments, clamps, saws, and the like. The term surgical instrument as used herein is defined to include a metallic part of a surgical instrument. The needles and instruments may have interior surfaces as well as exterior surfaces.

The oxide layers produced by the plasma treatment blackening process of the present invention will be sufficiently thick to effectively produce a conventional blue/black to black, non-reflective coating over the metal surface.

The following example is illustrative of the principles and practice of the present invention.

EXAMPLE

Approximately 1000 surgical needles made from 455 metal alloy were placed into the chamber of a Gasonics® Plasma Unit. The chamber had a volume of about 4 $ft^3$. The door to the unit was sealed and the chamber was evacuated under a vacuum of about 0.15 Torr for about one minute to purge volatiles and contaminants. The chamber was next back-filled with a mixture of 50 cc/minute of oxygen and 50 cc/minute of helium to a pressure of about 0.3 to about 0.5 Torr. The gaseous mixture was maintained in the chamber prior to switching power on for about 2 minutes. Next, power was switched on to the unit and the needles were exposed to the resulting gaseous plasma which was maintained at a power level of about 1000 watts for amount 90 minutes. Next, the power was switch off and the gaseous mixture was evacuated from the chamber. Next, the chamber was filled with nitrogen and held at a pressure of about 1.0 Torr for approximately 3–5 minutes until the needles were cool enough to be handled. The needles were then removed from the chamber of the gas plasma unit. Upon inspection, the surface of the needles were observed to have a conventional blue/black to black non-reflective appearance.

The processes of the present invention for blackening the surfaces of metal alloy surgical needles and surgical instruments have many advantages. Surprisingly and unexpectedly, it is now possible to blacken the surfaces of metal alloy surgical needles and surgical instruments in a controlled process which does not utilize chemical or electrochemical baths and which does not generate the associated fumes, emissions and hazardous waste streams. In addition, the use of high amperage electrical currents in order to electrically blacken needles is eliminated. Yet another advantage of the present invention is that needles which are processed in the gas plasma processes of the present invention are not subjected to the metal removal which is a characteristic disadvantage of the chemical or electrochemical processes. Still yet another advantage of the process of the present invention is that it is significantly more economical and cost effective than the prior art conventional blackening processes. The process of the present invention also eliminates the safety deficiencies associated with the conventional blackening processes.

Although this invention has been shown and described with respect to detailed embodiments thereof, it will be understood by those skilled in the art that various changes in form and detail thereof may be made without departing from the spirit and scope of the claimed invention.

We claim:

1. A method of blackening the surface of a metallic surgical needle, the method comprising:

exposing a metallic surgical needle having an exterior surface to a gaseous plasma for a sufficient period of time at a sufficient temperature to effectively produce a layer of an oxide of the metal sufficiently thick to provide a blackened color to the exterior surface.

2. The method of claim 1 wherein the gaseous plasma comprises a mixture of oxygen and helium and carbon tetrafluoride.

3. The method of claim 1 wherein the gaseous plasma comprises a mixture of oxygen, argon and carbon tetrafluoride.

4. The method of claim 1 wherein the plasma mixture comprises about 50 wt. % to about 99 wt. % of oxygen and about 1 wt. % to about 50 wt. % of helium and about 1 wt % to about 40 wt. % of carbon tetrafluoride.

5. The method of claim 1 wherein the metallic needle comprises an alloy selected from the group consisting of T-420 stainless steel, T-F stainless steel, T-455 stainless steel, and titanium nickel martensitic stainless steel alloy.

6. The method of claim 1 wherein the gaseous plasma is excited by an energy source, wherein said energy source comprises a member selected from the group consisting of Radio Frequency, Microwave and DC Discharge.

7. The method of claim 1 wherein the plasma comprises oxygen.

8. The method of claim 1 wherein the gaseous plasma comprises a mixture of oxygen and carbon tetrafluoride.

9. A method of blackening the surface of a metallic surgical instrument, the method comprising:

exposing a metallic surgical instrument having an exterior surface to a gaseous plasma for a sufficient period of time at a sufficient temperature to effectively blacken the exterior surface of the metallic surgical instrument.

10. The method of claim 9 wherein the gaseous plasma comprises a mixture of oxygen and helium and carbon tetrafluoride.

11. The method of claim 9 wherein the gaseous plasma comprises a mixture of oxygen and argon and carbon tetrafluoride.

12. The method of claim 9 wherein the plasma mixture comprises about 50 wt. % to about 99 wt. % of oxygen and about 1 wt. % to about 50 wt. % of helium and about 1 wt. % to about 40 wt. % of carbon tetrafluoride.

13. The method of claim 9 wherein the metallic surgical instrument comprises an alloy selected from the group consisting of T-420 stainless steel, T-F stainless steel, T-455 stainless steel, and titanium nickel martensitic stainless steel alloy.

14. The method of claim 9 wherein the gaseous plasmas is excited by an energy source, wherein said energy source comprises a member selected from the group consisting of Radio Frequency, Microwave and DC Discharge.

15. The method of claim 9 wherein the plasma comprises oxygen.

16. The method of claim 9 wherein the metallic surgical instrument additionally comprises at least one interior surface, and the interior surface is also blackened.

17. The method of claim 1 wherein the needle additionally comprises at least one interior surface, and the interior surface is also blackened.

18. The method of claim 9 wherein the gaseous plasma comprises a mixture of oxygen and carbon tetrafluoride.

19. The method of claim 9 wherein the gaseous plasma comprises a mixture of oxygen and helium.

20. A method of blackening the surface of a metallic surgical needle, the method comprising:

exposing a metallic surgical needle having an exterior surface to a gaseous plasma mixture for a sufficient period of time at a sufficient temperature to effectively produce a layer of an oxide of the metal sufficiently thick to provide a blackened color to the exterior surface, wherein the plasma mixture comprises about 50 wt. % to about 99 wt. % of oxygen and 1 wt. % to about 50 wt. % of helium and about 1 wt. % to about 40 wt. % of carbon tetraflouride, and wherein the metallic needle comprises an alloy selected from the group consisting of T-420 stainless steel, T-F stainless steel, T-455 stainless steel, and titanium nickel martensitic stainless steel alloy.

* * * * *

UNITED STATES PATENT AND TRADEMARK OFFICE
CERTIFICATE OF CORRECTION

PATENT NO. : 5,944,919
DATED : August 31, 1999
INVENTOR(S) : Robert Vetrecin, Bruce Hersey It is certified that error appears in the above-indentified patent and that said Letters Patent is hereby corrected as shown below:

Column 6, Line 52:

Now reads "oxygen and 1 wt. % to"

Should read: "oxygen and about 1 wt. % to"

Signed and Sealed this

Seventh Day of March, 2000

Attest:

Attesting Officer

Q. TODD DICKINSON
Commissioner of Patents and Trademarks